United States Patent [19]

Applezweig et al.

[11] Patent Number: 4,871,726
[45] Date of Patent: Oct. 3, 1989

[54] INCREASING THE BIOAVAILABILITY OF ALPHA-ETIOCHOLANOLONE

[75] Inventors: Norman Applezweig, New York; H. Leon Bradlow, Holliswood, both of N.Y.

[73] Assignee: Progenics, Inc., New York, N.Y.

[21] Appl. No.: 78,610

[22] Filed: Jul. 28, 1987

[51] Int. Cl.$^4$ ........................................... A61K 31/56
[52] U.S. Cl. ..................................................... 514/177
[58] Field of Search ......................................... 514/177

[56] References Cited

U.S. PATENT DOCUMENTS 4,666,898 5/1987 Coleman et al. ..................... 514/177

OTHER PUBLICATIONS

"Relative Effectiveness of Various Steroids in an Androgen Assay...", Cesare Cavallero et al., Acta Endocrinologica, 55 (1967), 135-135.

"Synthesis of Nucleic Acids by Isolated Nuclei: Effect of testosterone...", Biochem. Biophys. Acta, 202 (1970), 192-194.

"Tissue Effects of Glucocorticoids", J. D. Baxter et al., The American Journal of Medicine, vol. 53, Nov. 1972, pp. 573-589.

"Effect of Estrone and Progesterone on the Nuclear Uptake of Estradiol by Human Endometrium", by L. Tseng et al., Endo, 1973, vol. 93, No. 1.

"The Intranuclear Binding of Testosterone and 5α-Androstan...", by N. Bruchovsky et al., The Journal of Biological Chemistry, vol. 243, No. 22, Nov. 25, 1968, pp. 5953-5960.

"Steroids Prehormones", by D. Baird et al., Perspectives in Biology and Medicine, Spring 1968, pp. 384-421.

"Dynamics of Androgen Metabolism in Women with Hirsutism", by C. W. Bardin et al., Anals of Clinical Research 2: 251-262, 1970.

Primary Examiner—Frederick E. Waddell
Attorney, Agent, or Firm—Ostrolenk, Faber, Gerb & Soffen

[57] ABSTRACT

Methods and compositions are disclosed for inducing an increased blood level of alpha-etiocholanolone in the body of a mammal in need of such treatments comprising administering to said mammal an amount of etiocholanedione effective to induce said increased blood level.

18 Claims, 2 Drawing Sheets

INCREASING THE BIOAVAILABILITY OF ALPHA-ETIOCHOLANOLONE

FIELD OF THE INVENTION

This invention relates to methods and compositions for increasing the bioavailability of alpha-etiocholanolone, and their use in treating pathological conditions such as diabetes, obesity, and bone marrow suppressive disorders (which include but are not limited to aplastic anemia, bone marrow suppression due to the administration of cytotoxic chemotherapeutic agents, radiation exposure and anemias due to underproduction of erythropoietin, as in kidney dialysis patients).

BACKGROUND OF THE INVENTION

The steroid dehydroepiandrosterone (17 betahydroxyandrost-4-en-3-one, DHEA) and its sulfate derivatives are major steroid adrenal secretory products in humans. DHEA is metabolized to androsterone (3-alpha-hydroxy-5 alpha-androstan-17-one) and estradiol (Estra-1, 3, 5 (10)-triene-3, 17-diol), two major sex hormones in humans. Other metabolites of DHEA include alpha-etiocholanolone (5-betaandrostan-3-alpha-ol-17-one, hereinafter referred to as alpha-ET) and beta-etiocholanolone (5-beta-androstan-3-betaol-17-one, hereinafter referred to as beta-ET) and were, until recently, considered to be inert metabolic end products which were merely conjugated as glucuronides or sulfates and excreted in the urine. The structure of DHEA, alpha-ET, beta-ET and androsterone are shown in FIG. 1. Alpha-ET is the major metabolite of DHEA, and in normal individuals, is excreted in the urine in amounts of about 3–5 mg per day, whereas beta-ET is a minor metabolite in man.

Yen, et al. (*Lipids* 12:409, 1977) disclosed that DHEA, administered by a variety of routes, decreased the rate of weight gain in a strain of genetically obese mice. Coleman, et al. (*Diabetes* 31:830, 1982) demonstrated that DHEA treatment had a marked preventive effect on the development of diabetes in either genetically obese or diabetic mice. Furthermore, they indicated that for the maximal beneficial effect, DHEA had to be injested. This suggested that DHEA itself was not the active compound, but that some metabolite of DHEA produced during passage of the steroid through the gastrointestinal tract, was responsible for the activity. Coleman, et al. (*Endocrinology* 115:239–243, 1984) disclosed that alpha-ET and beta-ET, but not androsterone or epiandrosterone (see FIG. 1 for structure), were four times more effective than DHEA in preventing the development of diabetes in C57BL/KsJ-db/db diabetic mice. Alpha-ET and beta-ET reduced blood sugar, increased plasma insulin concentrations and provided a protective effect on the pancreas, as shown by an increase in the number of granulated islet beta-cells. These results demonstrated that both compounds had physiological significance and were not merely end products of sterol metabolism.

Coleman, et al. (U.S. Pat. No. 4,518,595, incorporated by reference) disclosed that oral administration of DHEA restored hyperglycemia to normal levels and improved glucose tolerance even in severely diabetic mammals. Coleman, et al. (U.S. Pat. No. 4,507,289, incorporated by reference) taught the use of alpha- and/or beta-ET and an estrogen for the treatment of diabetes, obesity syndromes and associated hypercorticoidism. Hypercorticoidism is a condition characterized by excessive functional activity of the adrenal cortex, caused by an excess of adrenalcorticotropic hormone (ACTH). This can lead to Cushing's syndrome, which is characterized by obesity, hypertension, diabetes and other symptoms. It has been proposed that the natural decline in DHEA levels with age produces a relative hypercorticoidism because of the imbalance between circulating levels of DHEA and the corticosteroids. This imbalance may affect a number of regulatory systems. Restoration of DHEA levels may therefore be beneficial in treating some of the diseases of aging, including diabetes and obesity. The activity of alpha-ET and beta-ET suggests that DHEA may actually be exerting its effects through their metabolites. The advantage of alpha-ET and beta-ET over DHEA is that they cannot be converted to estrogenic or androgenic hormones.

Coleman (*Endocrinology* 117:2279–2283. 1985) disclosed that alpha-ET and beta-ET, when supplied in the diet, have anti-obesity properties. They were effective both in preventing and in arresting the development of obesity as well as in facilitating weight reduction after obesity had been established in diabetic, genetically obese and normal mice. Finally, U.S. patent application Ser. No. 683,423, filed November 21, 1985 of Coleman and Applezweig discloses the use of etiocholanolones for the treatment of obesity, diabetes and other symptoms of hypercorticoidism.

Etiocholanolones have also been shown to participate in the regulation of porphyrin and heme synthesis in hepatic and erythroid cells (Granick, et al., *Proc. Nat. Acad. Sci. U.S.A.*, 57:1463, 1967) and act as inducers of porphyrin synthesis (Wolff, et al., *Ann. Int. Med.*, 67: 1268–1295, 1967).

Gardner and Juneja (*Brit. J. Hemat.*, in press, 1986) treated aplastic anemia patients with either alpha- and/or beta-ET. In this uncontrolled pilot study, 11 of the patients were considered to have acute severe aplasia, and 32 were considered chronic. Seventeen of the patients treated with alpha-ET had hematologic responses lasting longer than six months. (6 out of 11 acute; 11 out of 32 chronic patients). The patients maintained a normal hemoglobin level for long periods of time, and the effects persisted after the alpha-ET was discontinued. However, alpha-ET had been shown to produce acute pyrogenic reactions in man when administered by intramuscular (i.m.) injection (Kappas, et al., *J. Clin. Endocr.*, 16:948, 1956; Kappas, et al., *Trans. Assn. Am. Phys.*, 72:54, 1959). A concomitant dose of prednisolone was therefore used along with therapeutic injections of alpha-ET to prevent the development of fever and alleviate local irritation at the injection sites. Three patients who did not respond to alpha-ET had a hematologic recovery when treated with beta-ET. Moreover, the beta isomer had little pyrogenic effect and a dose of 10 mg of prednisolone was sufficient to counteract any local irritation.

The biological responses obtained in studies with alpha-ET and beta-ET have been correlated with the levels of free alpha-ET circulating in the blood. The use of alpha-ET and beta-ET to achieve therapeutic levels of alpha-ET in the blood has drawbacks, however, because they are rapidly removed from the body by conjugation and excretion, and they are relatively poorly absorbed by the oral route of administration. A means for improving alpha-ET blood levels therefore has the potential to provide superior therapeutic efficiency.

Previous work has suggested that alpha-ET and beta-ET are involved in complex metabolic processes in addition to conjugation and excretion. Administration of alpha-ET and beta-ET i.m. or intravenously [i.v.]to human subjects by Kappas, et al. (J. Clin. Endocr. 16:948, 1956) resulted in the recovery of almost exclusively alpha-ET conjugates in the urine, indicating a transformation of beta-ET to alpha-ET. Bradlow, et al. (J. Clin. Endocr. 27:1203–1207, 1967) found evidence for a rapid oxidation and re-reduction at the C-3 position of a portion of the alpha-ET administered i.v. to human subjects, based on isotopic ratios. A small portion of the alpha-ET also appeared to have a longer lifetime during which it continued to participate in oxidation-reduction systems and, possibly, served as a pool for which other metabolites of alpha-ET were derived. The full nature of the metabolic fate of alpha-ET was unknown at that time and none of the metabolites involved in the process were identified.

The present inventors have now unexpectedly discovered that both alpha-ET and beta-ET administered orally or parenterally (intraperitoneally, [i.p.], i.m. or i.v.) are rapidly oxidized at the C-3 position to form etiocholanedione (5 beta-androstanedione, hereinafter referred to as ET-dione) as shown in FIG. 2, and that ET-dione can serve as a superior source of circulating blood levels of free (nonconjugated) alpha-ET. Once formed, the ET-dione is re-reduced to alpha-ET, which may then be conjugated and excreted. This dynamic interconversion of alpha-ET and ET-dione provides the means of achieving alpha-ET blood levels through the use of ET-dione serving as a pro-drug for alpha-ET. In addition, whereas conjugation and excretion rapidly removes alpha-ET from the blood stream, ET-dione must be reduced to alpha-ET before being eliminated from the body, and may therefore have a longer circulatory half-life than alpha-ET.

Animal and human pharmacokinetic data demonstrate that ET-dione produces increased blood levels of free alpha-ET. This increased bioavailability may be due to improved absorption of ET-dione over alpha-ET. Although the present inventors do not wish to be bound by theory, another possibility is that the superior nature of the ET-dione is due to the fact that the molecule must be reduced to alpha-ET before conjugation-excretion occurs. By administering ET-dione, a reservoir of a precursor to alpha-ET can be established in the blood.

The present inventors have also found that administration of alpha-ET, beta-ET or ET-dione in oil substantially increased the amount of free circulating alpha-ET. This is a further means for increasing the bioavailability of this clinically important steroid.

OF THE INVENTION

The present invention has several objects including, but not limited to, the following:

- to increase the understanding of the role and nature of etiocholanedione and to use this for the treatment of human diseases;
- to devise methods and compositions for increasing the bioavailability of alpha-ET in the body of a mammal whereby anti-obesity, anti-diabetes and anti-bone marrow suppressive amounts of alpha-ET are released for a prolonged period of time in a sustained fashion using etiocholanedione.

These and other objects of the present invention will be apparent to those skilled in the art in light of the present description, accompanying claims and appended drawings.

SUMMARY OF THE INVENTION

One aspect of the present invention is directed to a method for inducing an increased blood level of alpha-etiocholanolone in the body of a mammal in need of such treatment, comprising administering to said mammal an amount of etiochololanedione effective to induce said blood level.

Another aspect of the present invention is directed to a method for treating a condition selected from the group conisting of obesity, diabetes syndromes, diabetes-associated hypercorticoidism and combinations thereof comprising administering an obesity- diabetes- or hypercorticoidism-antagonistic amount of etiocholanedione.

Yet another aspect of the present invention relates to a method for treating aplastic anemia and related bone marrow suppressive disorders comprising administering to a mammal an aplastic anemia- or bone marrow-suppressive antagonistic amount of etiocholanedione.

A further aspect of the present invention is directed to a composition for inducing an increased blood level of alpha-etiocholanolone in the body of a mammal in need of such treatment, said composition comprising an amount of etiocholanedione effective to induce said blood level and a pharmaceutically acceptable carrier.

DETAILED DESCRIPTION OF THE INVENTION

In accordance with the present invention, ET-dione is administered to a mammal in order to treat obesity, diabetes, associated hypercorticoidism and bone marrow suppressive disorders such as aplastic anemia.

Figure 1:
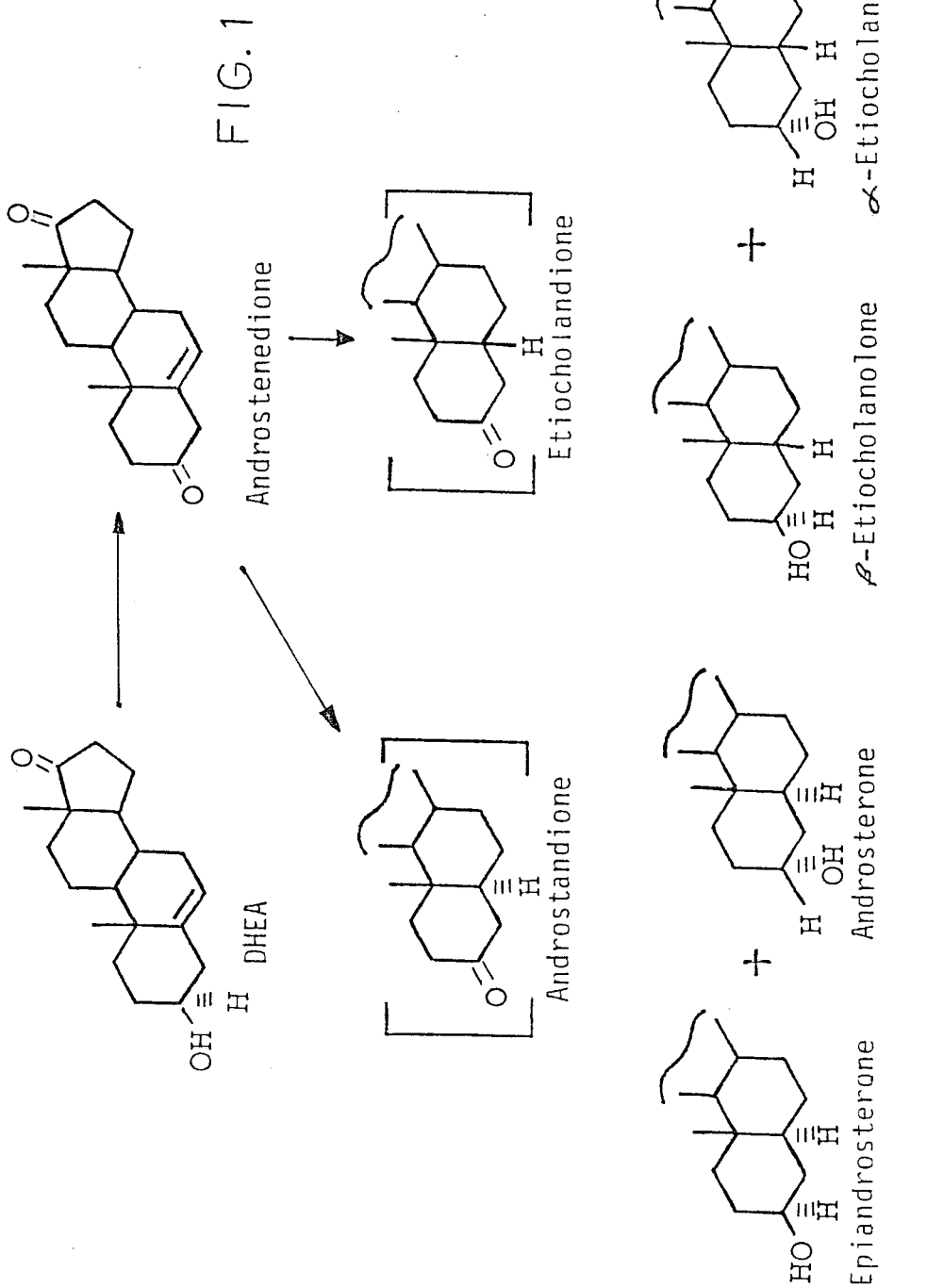
FIG. 1 shows the structures of the family of steroids of the present invention.
Figure 2:
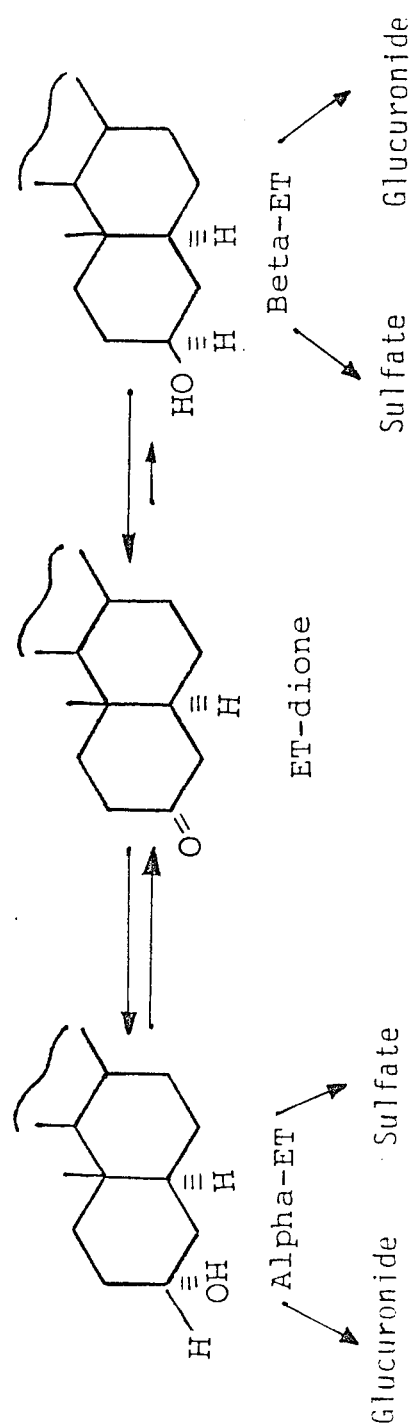
FIG. 2 depicts the interconversion of alpha-ET, beta-ET and ET-dione.

The present inventors have now discovered that alpha-ET or beta-ET administered, either orally or parenterally, are rapidly oxidized at the C-3 position to ET-dione. Furthermore, the inventors have found that following the conversion to dione, the dione is reconverted to alpha-ET. The dione is absorbed rapidly and circulates in the blood for a longer period of time than does alpha-ET since it is not subject to rapid conjugation and excretion in the urine. Its only access to excretion would be by reconversion to alpha-ET and conjugation. This is shown in FIG. 2. Thus, ET-dione can serve as a pro-drug for the maintenance of alpha-ET blood levels.

The reconversion of the dione to alpha-ET has been confirmed by administration of oral dosages of ET-dione by admixture with the diet (0.367%) over a period of three weeks to rats. The radioimmunoassay (RIA) for alpha-ET rose from approximately 40 nanograms per deciliter to approximately 600 nanograms per deciliter at the end of the three week feeding program. In humans, the present inventors have found that oral dosages of ET-dione lead to significantly enhanced blood levels of alpha-ET over equivalent dosages of alpha-ET (Table 1). In addition, ET-dione costs approximately one-third of what alpha-ET costs and is equally or, in some cases, almost 100% more effective. All of the above considerations make ET-dione not only suitable but preferred in the treatment of diabetes, obesity and blood suppressive disorders such as aplastic anemia.

Compositions containing ET-dione are administered either orally or parenterally. When administered orally, ET-dione and compositions containing ET-dione can be administered in a finely dispersed powder or solution which can be mixed with the food diet, or alternatively can be administered in tablet form. Compositions for i.p. injection would generally comprise serum albumin propylene glycol and other well-known agents as diluents and/or carriers. Average dosages of ET-dione, present in these composition would broadly range between about 1 and 1000 mg and preferably between about 10 and 500 mg per dosage form.

Average dosages of ET-dione for the treatment of diabetes, obesity, hypercorticoidism and/or bone marrow suppressive disorders would broadly range between about 1 to about 100 mg/kg, and preferably between about 20 and 70 mg/kg body weight for rats or mice. For humans, the average dosage would broadly range between about 0.1 to about 100 mg/kg, and preferably between about 20 and about 40 mg/kg body weight.

In the experiments described below, the alpha-ET, beta-ET and ET-dione were obtained from Steraloids (Wilton, NH) or alternatively could have been purchased from Houba (Culver, IN) or Chemodynamics (Garfield, NJ).

The absorption and blood level profiles of alpha-ET, beta-ET and ET-dione administered as oral suspensions to eight normal human volunteers were studied in a three-way crossover design study. Each subject received all three drugs in randomized order with a one-week wash-out period between doses. Following an overnight fast, subjects received 200 mg of test drug suspended in approximately 6 oz of apple juice. Blood samples were drawn immediately prior to drug administration and at 15 minutes, 30 minutes, 1, 2, 4, 8, 12 and 24 hours. Serum was obtained and analyzed for the level of alpha-ET by radioimmunoassay using antibodies commercially available from InterSci Diagnostics (Los Angeles, Calif.). The data is summarized in Table 1 below.

TABLE 1

FREE ALPHA-ET BLOOD LEVELS FROM ORAL ADMINISTRATION OF ALPHA-ET, BETA-ET AND ET-DIONE SUSPENSIONS

ALPHA-ET BLOOD LEVEL (ng/dl)

|  | Sample Time (Hr.) | Alpha-ET Blood Level (Mean) |
|---|---|---|
| ALPHA-ET |  |  |
|  | 0 | 21.5 |
|  | 0.25 | 2044 |
|  | 0.5 | 1915 |
|  | 1 | 1234 |
|  | 2 | 526 |
|  | 4 | 183 |
|  | 8 | 91 |
|  | 12 | 44 |
|  | 24 | 25 |
| BETA-ET |  |  |
|  | 0 | 16 |
|  | 0.25 | 600 |
|  | 0.5 | 909 |
|  | 1 | 836 |
|  | 2 | 401 |
|  | 4 | 129 |
|  | 8 | 65 |
|  | 12 | 30 |
|  | 24 | 25 |
| ET-DIONE |  |  |
|  | 0 | 12 |
|  | 0.25 | 3033 |
|  | 0.5 | 2563 |
|  | 1 | 1649 |
|  | 2 | 674 |
|  | 4 | 209 |
|  | 8 | 99 |
|  | 12 | 41 |
|  | 24 | 23 |

From the data summarized in Table 1, it can be seen that administration of ET-dione via the oral route led to significantly higher amounts of alpha-ET during the early time periods of from 15 minutes to approximately 1 hour after administration of the steroids; the blood levels declined rapidly in the next 1 to 2 hours, followed by a second slower phase. The half-life of the elimination in this second phase is similar to those determined for the blood levels of alpha-ET in conjugated form (presumably with sulfates and/or glucuronides). The present inventors have analyzed this phenomenon and have found that, at the 30 minutes post-administration, the levels of conjugated alpha-ET were 2-5 times higher than the free alpha-ET levels; this ratio increased at four hours due to the initially shorter half-life of the free drug.

At four hours past administration, the free alpha-ET levels from ET-dione were significantly higher than from alpha-ET or beta-ET administration, indicating that ET-dione can provide a reservoir for sustained alpha-ET levels.

The present invention is further described below by reference to specific examples, which are intended to illustrate the present invention without limiting its scope.

EXAMPLE 1

Weight gain in C57BL/6 genetically diabetic and obese mice fed alpha-ET, beta-ET or ET-dione Inhibition of the development of obesity was studied in two mutant mouse strains used for diabetes evaluation: C57BL/6, and C3HeB/FeJ ($A^{vy}/A$). Four-week old C57BL/6 and $A^{vy}/A$ mice were fed alpha-ET or ET-dione in order to evaluate their effects on diabetes and obesity. C57BL/6 mice (Jackson Laboratories, Bar Harbor, ME) display the genetic obesity syndrome markers obese (ob) and diabetes (db). $A^{vy}/A$ mice (Jackson Laboratories, Bar Harbor, ME) are characterized by mild obesity and an enhanced susceptibility to certain tumors. The data are summarized below in Tables 2 and 3.

TABLE 2

| WEIGHT GAIN IN C57BL/6 MICE (grams) | | | |
|---|---|---|---|
| TREATMENT | 2 WKS | 4 WKS | 8 WKS |
| Expt. 1 | | | |
| None | 13.0 | 19.0 | 25.6 |
| Alpha-ET 0.1% | 9.9 | 14.8 | 22.1 |
| Beta-ET 0.1% | 6.5 | 12.1 | 19.6 |

TABLE 2-continued

| WEIGHT GAIN IN C57BL/6 MICE (grams) | | | |
|---|---|---|---|
| TREATMENT | 2 WKS | 4 WKS | 8 WKS |
| Expt. 2 | | | |
| None | 9.9 | 15.4 | 22.9 |
| ET-dione 0.4% | 5.0 | 11.6 | 17.3 |

TABLE 3

| WEIGHT GAIN IN A$^{vy}$/A MICE (grams) | | | |
|---|---|---|---|
| TREATMENT | 2 WKS | 4 WKS | 6 WKS |
| Expt. 1 | | | |
| None | 9.2 | 18.2 | 26.9 |
| Alpha-ET 0.1% | 3.7 | 7.4 | 11.9 |
| Beta-ET 0.1% | 5.7 | 9.5 | 14.7 |
| Expt. 2 | | | |
| None | 11.2 | 18.1 | 26.6 |
| ET-dione 0.4% | 4.0 | 7.9 | 12.9 |

Groups of 8 male A$^{vy}$/A mice; mice fed ET-dione received 0.2% for six days during week 4 and were then returned to the 0.4% dose level In C57BL/6 mice, 0.1% alpha-ET and 0.1% beta-ET reduced weight gain from controls. ET-dione, at 0.4%, ingested for 8 weeks, reduced weight gain in a manner similar to alpha- and beta-ET as shown above in Table 2.

Similar results were obtained in obese A$^{vy}$/A mice. 0.4% ET-dione was again comparable in effectiveness to 0.1% alpha- and beta-ET (Table 3).

EXAMPLE 2

Effects of ET-dione and alpha-ET on weight gain in normal rats

Normal male Sprague-Dawley rats (Charles River Breeding Laboratory, Wilmington, MA) with an initial weight of 260±3 gms were allowed free access to a diet formulated to promote rapid weight gain (corn starch 15%, sucrose 15%, casein 20%, corn oil 5%, cellulose 5%, mineral mix 3.5%, vitamin mix 1%, DL-methionine 0.3%, and choline bitartrate 0.2%). Groups of ten rats were treated for three weeks with ET-dione, 0.367%, or alpha-ET, 0.2%, mixed in the diet or with diet alone. Food consumption and body weight were measured weekly. Blood samples were taken at the end of the study for assay of alpha-ET by RIA and measurement of serum total cholesterol, HDL-cholesterol and triglycerides. Liver weight (absolute and % of body weight), total cholesterol, % of esterified cholesterol and triglycerides in the liver were also determined. In addition, epididymal fat pad weights were measured.

The results are summarized below in Tables 4 and 5.

TABLE 4

| WEIGHT GAIN IN SPRAGUE-DAWLEY RATS FED ALPHA-ET OR ET-DIONE | | | | | | |
|---|---|---|---|---|---|---|
| | CONTROL | | Alpha-ET 0.2% | | ET-dione 0.367% | |
| Day | Weight(g) | W(g) | Weight(g) | W(g) | Weight(g) | W(g) |
| 0 | 260 ± 3* | — | 260 ± 3 | — | 260 ± 3 | — |
| 7 | 308 ± 5 | 48 | 301 ± 6 | 41 | 298 ± 2 | 38 |
| 14 | 354 ± 6 | 94 | 342 ± 8 | 82 | 341 ± 3 | 81 |
| 21 | 381 ± 7 | 121 | 368 ± 9 | 108 | 361 ± 3 | 101+ |
| | CONTROL | | Alpha-ET 0.2% | | ET-dione 0.367% | |
| % W vs | — | | −10.8% | | −16.6% | |

TABLE 4-continued

| WEIGHT GAIN IN SPRAGUE-DAWLEY RATS FED ALPHA-ET OR ET-DIONE | | | |
|---|---|---|---|
| Control Day 21 | | | |
| Fat Pad Wt(g) | 3.88 ± 0.29 | 3.06 ± 0.26+ | 3.50 ± 0.26 |
| Fat Pad as % of Body Wt | 1.02 ± 0.08 | 0.83 ± 0.04+ | 0.97 ± 0.07 |
| Alpha-ET Blood Level (ng/dl)** | 35 | 1590 | 1750 |

*Mean weight in grams ± S.E.
**Measured by RIA; sample taken at sacrifice (following a non-feeding period).
+Significantly different from control (p 0.05)

TABLE 5

| FOOD CONSUMPTION BY SPRAGUE-DAWLEY RATS FED ALPHA-ET OR ET-DIONE | | | |
|---|---|---|---|
| | FOOD CONSUMPTION (g/rat/day) | | |
| WEEK | CONTROL | ALPHA-ET 0.2% | ET-DIONE |
| 1 | 26.8 ± 0.8* | 24.7 ± 0.8 | 23.0 ± 0.6 |
| 2 | 24.9 ± 0.6 | 22.6 ± 0.9 | 24.6 ± 0.5 |
| 3 | 25.0 ± 0.6 | 23.1 ± 0.8 | 22.6 ± 0.5 |
| Average | 25.6 ± 0.6 | 23.5 ± 0.6 | 23.4 ± 0.6** |
| Food Efficiency+ | 0.236 | 0.230 | 0.217 |

*Means ± S.E.
**Significantly different from Control (p 0.05)
+Total weight gained (g) − food consumed (g) during study Treatment with 0.367% ET-dione resulted in a significantly lower weight gain than in controls (101 g vs 121 g) during the three weeks. The weight gain of the 0.2% alpha-ET treated group was also lower, but the differences were not significant in demonstrating the superior nature of the dione. The weight of the epididymal fat pads was significantly lower, however, in alpha-ET treated rats but not in ET-dione treated rats (Table 4).

Both ET-dione and alpha-ET reduced food consumption (Table 5); the food efficiency for ET-dione was still somewhat lower than controls (0.217 vs 0.236 gms body weight per gm food intake) and, again, superior to alpha-ET. The blood levels of alpha-ET produced by 0.2% alpha-ET and 0.367% ET-dione were similar (1590 and 1750 mcg per dl respectively). Since the blood was drawn after a fasting period of 8 to 10 hours, the measured levels are likely to be substantially lower than the average circulating levels during the study period.

A second study was carried out on male Sprague-Dawley rats with initial starting weight of 272±5 gms. Diet was modified to increase the fat content as follows: corn starch 19.4%, sucrose 34.6%, casein 22.2%, corn oil 8.9%, lard 8.9%, mineral mix 3.5% vitamin mix 2.2%, DL-methionine 0.3%. Groups of nine rats were treated for five weeks with diet alone, with the additional of alpha-ET at 0.2 or 0.4%, or ET-dione at 0.4 or 0.8%. On the last day of the study the animals were dosed with approximately 1 micro Ci of $^3$H labeled material (Amersham, Arlington Heights, IL) corresponding to the treatment they had received. Groups of three animals were sacrificed at 1 hour, 4 hours and 12 hours after dosing, and the adrenals, gonads, liver, epididymal fat pads, and blood collected for analysis. Urine and feces were also collected during the post-tracer dosing period. The data is presented below in Table 6.

TABLE 6
BODY WEIGHT GAINS & FOOD CONSUMPTION IN SPRAGUE-DAWLEY RATS TREATED WITH ALPHA-ET OR ET-DIONE

| | Control | 0.4% ET-Dione | 0.8% ET-Dione | 0.2% Alpha-ET | 0.4% Alpha-ET |
|---|---|---|---|---|---|
| Day | | | | | |
| 0 | — | — | — | — | — |
| 7 | 56 | 44 | 34 | 51 | 49 |
| 14 | 109 | 89 | 83 | 100 | 98 |
| 21 | 145 | 117 | 112 | 130 | 130 |
| 28 | 183 | 149 | 144 | 165 | 162 |
| % W vs Control Day 28 | — | −18.6% | −21.3% | −9.8% | −11.5% |
| FOOD CONSUMPTION (g/day) | | | | | |
| Week | | | | | |
| 1 | 25.4 ± 0.4 | 23.1 ± 0.7 | 20.4 ± 0.8 | 24.1 ± 0.4 | 23.5 ± 0.7 |
| 2 | 23.2 ± 0.8 | 21.4 ± 1.2 | 20.9 ± 0.9 | 20.9 ± 0.7 | 21.2 ± 0.5 |
| 3 | 23.3 ± 0.7 | 21.3 ± 1.0 | 19.9 ± 0.7 | 20.4 ± 0.6 | 20.8 ± 0.5 |
| 4 | 22.7 ± 1.0 | 22.3 ± 1.4 | 21.1 ± 0.6 | 21.3 ± 0.7 | 20.8 ± 0.8 |
| Av. Wks 1–4 | 23.4 | 22.0 | 20.6 | 21.7 | 21.6 |
| Food Efficiency | 0.279 | 0.250 | 0.272 | 0.272 | 0.268 |

Et-dione at 0.4% and alpha-ET at 0.2% produced reductions in weight gains. ET-dione was almost twice as effective as alpha-ET at all concentrations tested. In addition, ET-dione was equally effective as alpha-ET in reducing food consumption. The higher doses of ET-dione and alpha-ET did not produce substantial further decreases (Table 6).

EXAMPLE 3

The effect of oil on the uptake of alpha-ET, beta-ET and ET-dione

In an attempt to explore other ways to increase the bioavailability of alpha-ET, the present inventors examined the effects of oil on the uptake of alpha-ET, beta-ET and ET-dione. Six Balb/c mice per group, each 20 grams average weight, were administered the steroids by gavage dose in 0.3 mls of sesame oil. The results are presented below in Table 7.

TABLE 7

| | Dose | Alpha-ET blood level (mcg/dl) at | | | |
|---|---|---|---|---|---|
| | | 1 hr | 3 hrs | 8 hrs | 24 hrs |
| ET-dione | 10 mg | 376 | 256 | 218 | 3.6 |
| ET-dione | 5 mg | 180 | 199 | 46.4 | 3.2 |
| Alpha-ET | 5 mg | 197 | 185 | 60.8 | 4.8 |
| Beta-ET | 5 mg | 129 | 76 | 48 | 2.0 |

The date presented in Table 7 demonstrates that sesame oil significantly enhanced the absorption of all three steroids. The advantage of using the dione over alpha-ET or beta-ET was overcome by the use of sesame oil. Other alternative oils which can also be used to increase the uptake of these steroids are generally vegetable oils such as soy, corn and cotton seed.

In summary, ET-dione treatment leads to significant blood levels of alpha-ET, as demonstrated by both radioimmunoassay and biological effects. Effective alpha-ET levels can be maintained by administration of ET-dione. Due to the lower cost and either equal or increased biological effectiveness, ET-dione is well-suited for the treatment of obesity, diabetes bone marrow suppressive disorders such as and aplastic anemia.

The invention has been described above by reference to preferred embodiments. It is understood that many additions, deletions and modifications will be apparent to one of ordinary skill in the art in light of the present description without departing from the scope of the invention, as claimed below.

What is claimed is:

1. A method for treating a condition selected from the group consisting of obesity, diabetes syndrome, diabetes-associated hypercorticoidism and combinations thereof comprising administering to a mammal in need of such treatment an obesity-, diabetes- or hypercorticoidism-antagonistic amount of etiocholanedione.

2. The method of claim 1 comprising administering etiocholanedione orally or parenterally.

3. The method of claim 2 wherein the amount of etiocholanedione is within the range between about 1 and about 100 mg/kg body weight for rats or mice.

4. The method of claim 3 wherein said amount of etiocholanedione is within the range between about 20 and about 60 mg/kg body weight for rats or mice.

5. The method of claim 2, wherein the amount of etiocholanedione is within the range between about 0.1 to about 100 mg/kg body weight for humans.

6. The method of claim 5, wherein the amount of etiocholanedione is within the range between about 20 to about 40 mg/kg body weight for humans.

7. A method for treating bone marrow-suppressive disorders comprising administering to a mammal in need of such treatment a bone marrow suppression-antagonistic amount of etiocholanedione.

8. The method of claim 7 comprising administering etiocholanedione orally or parenterally.

9. The method of claim 8 wherein the amount of said etiocholanedione is within the range between about 1 and about 100 mg/kg body weight for rats or mice.

10. The method of claim 9 wherein the amount of said etiocholanedione is within the range between about 20 and about 60 mg/kg body weight for rats or mice.

11. The method of claim 7 wherein the amount of etiocholanedione is within the range between about 0.1 to about 100 mg/kg body weight for humans.

12. The method of claim 11 wherein the amount of etiocholanedione is within the range between about 20 to 40 mg/kg body weight for humans.

13. A composition for inducing an increased blood level of alpha-etiocholanolone in the body of a mammal in need of such treatment, said composition comprising an amount of etiocholanedione effective to induce said increased blood level and a pharmaceutically acceptable carrier.

14. The composition of claim 13 comprising a parenteral dosage form.

15. The composition of claim 13 comprising an oral dosage form.

16. The composition of claim 13 wherein the amount of etiocholanedione is within the range between about 1 and about 1000 mg per dosage form.

17. The composition of claim 13 further comprising an uptake-increasing effective amount of a pharmaceutically acceptable vegetable oil selected from the group consisting of sesame, soy and corn.

18. The composition of claim 17 wherein said oil is sesame oil.

* * * * *